(12) United States Patent  
Ethelfeld

(10) Patent No.: US 7,981,085 B2  
(45) Date of Patent: Jul. 19, 2011

(54) INTERNAL NEEDLE INSERTER

(75) Inventor: Erik Winkel Ethelfeld, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 129 days.

(21) Appl. No.: 11/266,905

(22) Filed: Nov. 4, 2005

(65) Prior Publication Data

US 2006/0142698 A1    Jun. 29, 2006

Related U.S. Application Data

(63) Continuation of application No. PCT/DK2004/000333, filed on May 10, 2004.

(60) Provisional application No. 60/471,010, filed on May 16, 2003.

(30) Foreign Application Priority Data

May 8, 2003 (DK) ................................ 2003 00697

(51) Int. Cl.
  *A61M 5/20* (2006.01)
  *A61M 5/00* (2006.01)
(52) U.S. Cl. ........................................ 604/157; 604/187
(58) Field of Classification Search ................ 604/157, 604/134–139, 187, 19, 21, 27, 36, 48, 93.01
  See application file for complete search history.

(56) References Cited

U.S. PATENT DOCUMENTS

| 55,711 A | 6/1866 | Regester |
|---|---|---|
| 69,546 A | 10/1867 | DeFrost |
| 123,740 A | 2/1872 | Stevens |
| 2,605,765 A | 8/1952 | Kollsman |
| 2,960,097 A | 11/1960 | Scheffler |
| 2,980,032 A | 4/1961 | Schneider |
| 3,705,601 A | 12/1972 | Arisland |
| 4,016,879 A | 4/1977 | Mellor |
| 4,077,405 A | 3/1978 | Haerten et al. |

(Continued)

FOREIGN PATENT DOCUMENTS

CA   2239457   12/1999

(Continued)

OTHER PUBLICATIONS

Non-Final Rejection Mailed on Jan. 5, 2007 in U.S. Appl. No. 11/266,904, filed Nov. 4, 2005 by Ethelfeld et al.

(Continued)

*Primary Examiner* — Theodore J Stigell
*Assistant Examiner* — Michael J Anderson
(74) *Attorney, Agent, or Firm* — Wesley A. Nicolas; Marc A. Began

(57) ABSTRACT

A device comprises a housing having a mounting surface adapted for application to the skin of a subject, a needle with a pointed end portion adapted to penetrate the skin the subject, the needle having a first position in which the distal end portion is retracted within the housing, and a second position in which the distal end portion projects relative to the mounting surface. The device further comprises actuatable driving means actuatable to cause activation as well as release of the driving means, thereby moving the needle from the first position to the second position. By this arrangement the needle device can be supplied to the user in a non-energized state, the energizing taking place when the device is actuated by the user which means that energy will be stored only for a period from a few seconds to a few hours or days.

4 Claims, 11 Drawing Sheets

U.S. PATENT DOCUMENTS

| | | | |
|---|---|---|---|
| 4,137,020 A | 1/1979 | Ito et al. | |
| 4,245,634 A | 1/1981 | Albisser et al. | |
| 4,262,824 A | 4/1981 | Hrynewycz | |
| 4,340,048 A | 7/1982 | Eckenhoff | |
| 4,370,305 A | 1/1983 | Affonso | |
| 4,378,015 A * | 3/1983 | Wardlaw | 604/137 |
| 4,399,824 A | 8/1983 | Davidson | |
| 4,402,407 A | 9/1983 | Maly | |
| 4,519,792 A | 5/1985 | Dawe | |
| 4,529,401 A | 7/1985 | Leslie et al. | |
| 4,544,369 A | 10/1985 | Skakoon et al. | |
| 4,552,561 A | 11/1985 | Eckenhoff et al. | |
| 4,645,491 A | 2/1987 | Evans | |
| 4,657,490 A | 4/1987 | Abbott | |
| 4,710,170 A | 12/1987 | Haber | |
| 4,734,092 A | 3/1988 | Millerd | |
| 4,753,651 A * | 6/1988 | Eckenhoff | 424/449 |
| 4,755,173 A | 7/1988 | Konopka et al. | |
| 4,788,556 A | 11/1988 | Hoisington et al. | |
| 4,871,351 A | 10/1989 | Feingold | |
| 4,877,034 A | 10/1989 | Atkins et al. | |
| 4,886,499 A * | 12/1989 | Cirelli et al. | 604/131 |
| 4,894,054 A | 1/1990 | Miskinyar | |
| 4,928,528 A | 5/1990 | Marques | |
| 4,994,078 A | 2/1991 | Jarvik | |
| 5,008,110 A | 4/1991 | Benecke et al. | |
| 5,049,146 A | 9/1991 | Bringham et al. | |
| 5,076,890 A | 12/1991 | Balembois | |
| 5,122,116 A | 6/1992 | Kriesel et al. | |
| 5,122,201 A | 6/1992 | Frazier et al. | |
| 5,149,340 A | 9/1992 | Waycuilis | |
| 5,169,390 A | 12/1992 | Athayde et al. | |
| 5,211,201 A | 5/1993 | Kamen et al. | |
| 5,224,843 A | 7/1993 | van Lintel | |
| 5,256,157 A | 10/1993 | Samiotes et al. | |
| 5,336,052 A | 8/1994 | Zöllner et al. | |
| 5,390,671 A | 2/1995 | Lord et al. | |
| 5,391,950 A | 2/1995 | Krawczak | |
| 5,482,473 A | 1/1996 | Lord et al. | |
| 5,485,917 A | 1/1996 | Early | |
| 5,494,415 A | 2/1996 | Morita | |
| 5,514,095 A | 5/1996 | Brightbill et al. | |
| 5,527,287 A | 6/1996 | Miskinyar | |
| 5,527,288 A | 6/1996 | Gross et al. | |
| 5,568,806 A | 10/1996 | Cheney, II et al. | |
| 5,584,808 A | 12/1996 | Healy | |
| 5,584,813 A | 12/1996 | Livingston et al. | |
| 5,586,085 A | 12/1996 | Lichte | |
| 5,609,572 A | 3/1997 | Lang | |
| 5,647,853 A | 7/1997 | Feldmann et al. | |
| 5,720,391 A | 2/1998 | Dohm et al. | |
| 5,776,109 A | 7/1998 | Urrutia | |
| 5,814,020 A * | 9/1998 | Gross | 604/141 |
| 5,851,197 A | 12/1998 | Marano et al. | |
| 5,858,001 A * | 1/1999 | Tsals et al. | 604/135 |
| 5,860,952 A | 1/1999 | Quinn | |
| 5,913,856 A | 6/1999 | Chia et al. | |
| 5,925,017 A | 7/1999 | Kriesel et al. | |
| 5,928,194 A | 7/1999 | Maget | |
| 5,931,814 A * | 8/1999 | Alex et al. | 604/131 |
| 5,941,611 A | 8/1999 | Trzmiel et al. | |
| 5,954,643 A | 9/1999 | VanAntwerp et al. | |
| 5,957,895 A * | 9/1999 | Sage et al. | 604/181 |
| 5,968,011 A | 10/1999 | Larsen et al. | |
| 5,997,501 A | 12/1999 | Gross et al. | |
| 6,045,534 A | 4/2000 | Jacobsen et al. | |
| 6,060,319 A | 5/2000 | Deetz et al. | |
| 6,074,369 A | 6/2000 | Sage et al. | |
| 6,083,196 A | 7/2000 | Trautman et al. | |
| 6,088,619 A | 7/2000 | Hein et al. | |
| 6,099,512 A | 8/2000 | Urrutia | |
| 6,120,492 A | 9/2000 | Finch et al. | |
| 6,123,519 A | 9/2000 | Kato et al. | |
| 6,126,637 A | 10/2000 | Kriesel et al. | |
| 6,132,755 A | 10/2000 | Eicher et al. | |
| 6,165,155 A | 12/2000 | Jacobsen et al. | |
| 6,241,704 B1 | 6/2001 | Peterson et al. | |
| 6,270,478 B1 | 8/2001 | Mernøe | |
| 6,280,148 B1 | 8/2001 | Zengerle et al. | |
| 6,293,925 B1 | 9/2001 | Safabash et al. | |
| 6,302,866 B1 | 10/2001 | Marggi | |
| 6,302,869 B1 | 10/2001 | Klitgaard | |
| 6,358,731 B1 | 3/2002 | Hsu | |
| 6,364,865 B1 | 4/2002 | Lavi et al. | |
| 6,485,461 B1 | 11/2002 | Mason et al. | |
| 6,500,150 B1 * | 12/2002 | Gross et al. | 604/131 |
| 6,551,276 B1 | 4/2003 | Mann et al. | |
| 6,554,791 B1 | 4/2003 | Cartledge et al. | |
| 6,555,986 B2 | 4/2003 | Moberg | |
| 6,558,351 B1 | 5/2003 | Steil et al. | |
| 6,589,229 B1 | 7/2003 | Connelly et al. | |
| 6,613,015 B2 | 9/2003 | Sandstrom et al. | |
| 6,622,037 B2 | 9/2003 | Kasano | |
| 6,656,159 B2 | 12/2003 | Flaherty | |
| 6,716,192 B1 | 4/2004 | Orosz | |
| 6,740,059 B2 | 5/2004 | Flaherty | |
| 6,749,587 B2 | 6/2004 | Flaherty | |
| 6,808,691 B1 | 10/2004 | Herve et al. | |
| 6,818,178 B2 | 11/2004 | Kohl et al. | |
| 6,878,136 B2 | 4/2005 | Fleury et al. | |
| 6,949,084 B2 | 9/2005 | Marggi et al. | |
| 6,960,192 B1 | 11/2005 | Flaherty et al. | |
| 7,052,483 B2 * | 5/2006 | Wojcik | 604/162 |
| 7,070,580 B2 | 7/2006 | Nielsen | |
| 7,097,631 B2 | 8/2006 | Trautman et al. | |
| 7,097,690 B2 | 8/2006 | Usher et al. | |
| 7,141,023 B2 | 11/2006 | Diermann et al. | |
| 7,144,384 B2 | 12/2006 | Gorman et al. | |
| 858,001 A1 | 6/2007 | Howe | |
| 7,303,073 B2 | 12/2007 | Raynal-Olive et al. | |
| 7,744,570 B2 | 6/2010 | Fangrow | |
| 2001/0025168 A1 | 9/2001 | Gross et al. | |
| 2002/0040083 A1 | 4/2002 | Kuwaki et al. | |
| 2002/0040208 A1 | 4/2002 | Flaherty et al. | |
| 2002/0055711 A1 | 5/2002 | Lavi et al. | |
| 2002/0064468 A1 | 5/2002 | Wade | |
| 2002/0123740 A1 * | 9/2002 | Flaherty et al. | 604/890.1 |
| 2002/0161332 A1 | 10/2002 | Ramey | |
| 2002/0169416 A1 | 11/2002 | Gonnelli et al. | |
| 2003/0009131 A1 | 1/2003 | Van Antwerp et al. | |
| 2003/0009133 A1 | 1/2003 | Ramey | |
| 2003/0029501 A1 | 2/2003 | Williamson et al. | |
| 2003/0060781 A1 | 3/2003 | Mogensen et al. | |
| 2003/0065308 A1 | 4/2003 | Lebel et al. | |
| 2003/0069546 A1 | 4/2003 | Sandstrom et al. | |
| 2003/0073952 A1 | 4/2003 | Flaherty et al. | |
| 2003/0088238 A1 | 5/2003 | Poulsen et al. | |
| 2003/0114797 A1 | 6/2003 | Vaillancourt et al. | |
| 2003/0135159 A1 | 7/2003 | Daily et al. | |
| 2003/0167035 A1 | 9/2003 | Flaherty et al. | |
| 2003/0187395 A1 | 10/2003 | Gabel et al. | |
| 2003/0194328 A1 | 10/2003 | Bryant et al. | |
| 2003/0199823 A1 | 10/2003 | Bobroff et al. | |
| 2003/0216686 A1 | 11/2003 | Lynch et al. | |
| 2003/0236498 A1 | 12/2003 | Gross et al. | |
| 2004/0051674 A1 | 3/2004 | Mahringer | |
| 2004/0087240 A1 | 5/2004 | Chen et al. | |
| 2004/0098068 A1 | 5/2004 | Carbunaru et al. | |
| 2004/0115068 A1 | 6/2004 | Hansen et al. | |
| 2004/0116905 A1 * | 6/2004 | Pedersen et al. | 604/890.1 |
| 2004/0127844 A1 | 7/2004 | Flaherty | |
| 2004/0158207 A1 | 8/2004 | Hunn et al. | |
| 2004/0162521 A1 | 8/2004 | Bengtsson | |
| 2004/0171403 A1 | 9/2004 | Mikkola | |
| 2004/0199123 A1 | 10/2004 | Nielsen | |
| 2004/0204673 A1 | 10/2004 | Flaherty et al. | |
| 2004/0220497 A1 * | 11/2004 | Findlay et al. | 600/562 |
| 2004/0220536 A1 | 11/2004 | VanTassel et al. | |
| 2004/0260233 A1 | 12/2004 | Garibotto et al. | |
| 2005/0006309 A1 | 1/2005 | Effenhauser et al. | |
| 2005/0022274 A1 | 1/2005 | Campbell et al. | |
| 2005/0077225 A1 | 4/2005 | Usher et al. | |
| 2005/0101933 A1 | 5/2005 | Marrs et al. | |
| 2005/0171513 A1 | 8/2005 | Mann et al. | |
| 2005/0203461 A1 | 9/2005 | Flaherty et al. | |
| 2005/0240154 A1 | 10/2005 | Mogensen et al. | |
| 2006/0015063 A1 | 1/2006 | Butikofer et al. | |

| | | | |
|---|---|---|---|
| 2006/0017576 A1 | 1/2006 | Gordon et al. | |
| 2006/0020300 A1 | 1/2006 | Nghiem et al. | |
| 2006/0142698 A1* | 6/2006 | Ethelfeld | 604/157 |
| 2006/0200073 A1 | 9/2006 | Radmer et al. | |
| 2006/0264835 A1 | 11/2006 | Nielsen et al. | |
| 2007/0021733 A1 | 1/2007 | Hansen et al. | |
| 2007/0073228 A1 | 3/2007 | Mernoe et al. | |
| 2007/0104596 A1 | 5/2007 | Preuthun et al. | |
| 2007/0112301 A1 | 5/2007 | Preuthun et al. | |
| 2008/0009805 A1 | 1/2008 | Ethefeld | |
| 2009/0163874 A1 | 6/2009 | Krag et al. | |

FOREIGN PATENT DOCUMENTS

| | | |
|---|---|---|
| CN | 1612758 | 5/2005 |
| DE | 2552446 | 5/1977 |
| DE | 10255817 | 6/2004 |
| DK | PA 2003 00696 | 5/2003 |
| DK | PA 2003 00697 | 5/2003 |
| EP | 20060277 | 3/1986 |
| EP | 398583 | 11/1990 |
| EP | 568176 | 11/1993 |
| EP | 937475 | 1/1999 |
| EP | 1177802 | 7/2001 |
| EP | 1177802 | 2/2002 |
| EP | 1256356 | 11/2002 |
| EP | 1329233 | 7/2003 |
| EP | 1475113 | 11/2004 |
| EP | 1527792 | 5/2005 |
| GB | 2020735 | 11/1979 |
| GB | 2212387 | 7/1989 |
| JP | 2000-104659 | 4/2000 |
| JP | 2000-513259 | 10/2000 |
| JP | 2000-515394 | 11/2000 |
| JP | 2002-505601 | 2/2002 |
| WO | WO 90/07942 | 7/1990 |
| WO | WO 96/07397 | 3/1996 |
| WO | WO 96/30679 | 10/1996 |
| WO | WO 97/21457 | 6/1997 |
| WO | WO 98/57683 | 12/1998 |
| WO | WO 99/62576 | 12/1999 |
| WO | WO 02/02165 | 1/2002 |
| WO | WO 02/04048 | 1/2002 |
| WO | WO02/05889 | 1/2002 |
| WO | 02/15965 | 2/2002 |
| WO | WO 02/15889 | 2/2002 |
| WO | WO 02/40083 | 5/2002 |
| WO | 02/47746 | 6/2002 |
| WO | WO0245574 | 6/2002 |
| WO | WO02/055132 | 7/2002 |
| WO | WO 02/070024 | 9/2002 |
| WO | WO02/081012 | 10/2002 |
| WO | WO02/100457 | 12/2002 |
| WO | WO03000696 | 1/2003 |
| WO | WO03000697 | 1/2003 |
| WO | WO03/026726 | 4/2003 |
| WO | WO03/026728 | 4/2003 |
| WO | WO 03/080169 | 10/2003 |
| WO | WO03/089028 | 10/2003 |
| WO | WO 03/090509 | 11/2003 |
| WO | WO 03/099358 | 12/2003 |
| WO | WO 2004/009160 | 1/2004 |
| WO | 2004/029457 | 4/2004 |
| WO | WO2004/030728 | 4/2004 |
| WO | WO2004/098682 | 11/2004 |
| WO | WO 2004/098683 | 11/2004 |
| WO | WO2004/098684 | 11/2004 |
| WO | WO 2004/101071 | 11/2004 |
| WO | WO2005/002649 | 1/2005 |
| WO | WO 2005/011779 | 2/2005 |
| WO | WO 2005/025652 | 3/2005 |
| WO | WO2005/037185 | 4/2005 |
| WO | WO2005/037350 | 4/2005 |
| WO | WO2005/039673 | 5/2005 |
| WO | WO2005/094919 | 10/2005 |
| WO | WO 2005/123186 | 12/2005 |
| WO | WO 2005/123189 | 12/2005 |
| WO | WO2006/060277 | 6/2006 |
| WO | WO 2006/067217 | 6/2006 |
| WO | WO 2006/077263 | 7/2006 |
| WO | WO2006/089958 | 8/2006 |
| WO | WO 2006/120253 | 11/2006 |
| WO | WO 2006/123329 | 11/2006 |
| WO | WO2007/122207 | 11/2007 |
| WO | WO 2009/021950 | 2/2009 |

OTHER PUBLICATIONS

Final Rejection Mailed on Sep. 11, 2007 in U.S. Appl. No. 11/266,904, filed Nov. 4, 2005 by Ethelfeld et al.
Final Rejection Mailed on Apr. 16, 2010 in U.S. Appl. No. 11/266,904, filed Oct. 4, 2005 by Erik Winkel Ethelfeld.
Non-Final Rejection Mailed on Nov. 27, 2009 in U.S. Appl. No. 11/266,904, filed Oct. 4, 2005 by Erik Winkel Ethelfeld.
Non-Final Rejection Mailed on Mar. 28, 2008 in U.S. Appl. No. 11/266,821, filed Nov. 4, 2005 by Erik Winkel Etiielfeld.
Final Rejection Mailed on Jul. 18, 2008 in U.S. Appl. No. 11/266,821, filed Nov. 4, 2005 by Erik Winkel Ethelfeld.
Non-Final Rejection Mailed on Jan. 29, 2009 in U.S. Appl. No. 11/266,821, filed Nov. 4, 2005 by Erik Winkel Etiielfeld.
English Abstract of JP2000-513259.
Machine Translation of JP2000-515394.
Machine Translation of JP2002-505601.
International Search Report mailed Jul. 5, 2007 in international application No. PCT/EP2007/053923.
International Preliminary Examination Report issued in connection with counterpart PCT Application No. PCT/EP2006/062301, mailed Nov. 22, 2007.
International Search Report and Written Opinion issued in connection with counterpart international application No. PCT/EP2006/062301, mailed Nov. 2, 2006.
International Search Report mailed May 24, 2006 in international application No. PCT/EP2006/050410.
Office Action Issued in Connection With Counterpart Danish Application No. PA 2005 00703, Mailed Mar. 3, 2006.
CN 1612758 English Abstract, published Feb. 6, 2008.
DE 10255817 English Abstract, published Jun. 17, 2004.
DE 2552446 English Abstract, published May 26, 1977.
JP 2000-104659 Machine Translation, published Apr. 11, 2000.
Final Office Action mailed Apr. 16, 2010 in U.S. Appl. No. 12/303,307, filed Feb. 20, 2009 by Krag.
Non-Final Office Action mailed Nov. 27, 2009 in U.S. Appl. No. 12/303,307, filed Feb. 20, 2009 by Krag.
Non-Final Office Action mailed Apr. 6, 2010 in U.S. Appl. No. 12/298,253, filed Dec. 8, 2008 by Krag et al.
Final Office Action mailed Apr. 28, 2010 in U.S. Appl. No. 12/066,712, filed Mar. 13, 2008 by Hansen et al.
Non-Final Office Action mailed Oct. 27, 2009 in U.S. Appl. No. 12/066,712, filed Mar. 13, 2008 by Hansen et al.
Non-Final Office Action mailed Apr. 10, 2009 in U.S. Appl. No. 12/066,712, filed Mar. 13, 2008 by Hansen et al.
Final Office Action mailed Jul. 16, 2010 in U.S. Appl. No. 11/913,689, filed Dec. 12, 2007 by Hansen et al.
Non-Final Office Action mailed Mar. 15, 2010 in U.S. Appl. No. 11/913,689, filed Dec. 12, 2007 by Hansen et al.
Final Office Action mailed Nov. 25, 2009 in U.S. Appl. No. 11/913,689, filed Dec. 12, 2007 by Hansen et al.
Non-Final Office Action mailed May 8, 2009 in U.S. Appl. No. 11/913,689, filed Dec. 12, 2007 by Hansen et al.
Non-Final Office Action mailed Apr. 30, 2010 in U.S. Appl. No. 11/911,213, filed Oct. 11, 2007 by Nielsen et al.
Non-Final Office Action mailed Jul. 24, 2009 in U.S. Appl. No. 11/911,213, filed Oct. 11, 2007 by Nielsen et al.
Final Office Action mailed Nov. 17, 2009 in U.S. Appl. No. 11/816,729, filed Nov. 15, 2007 by Larsen et al.
Non-Final Office Action mailed Apr. 17, 2009 in U.S. Appl. No. 11/816,729, filed Nov. 15, 2007 by Larsen et al.
Non-Final Office Action mailed Jul. 23, 2010 in U.S. Appl. No. 11/813,433, filed Apr. 30, 2008 by Teisen-Simony et al.
Non-Final Office Action mailed Apr. 28, 2010 in U.S. Appl. No. 11/813,381, filed Apr. 11, 2008 by Teisen-Simony et al.
Final Office Action mailed Nov. 3, 2009 in U.S. Appl. No. 11/792,355, filed Apr. 23, 2008 by Ethelfeld et al.

Non-Final Office Action mailed Feb. 17, 2009 in U.S. Appl. No. 11/792,355, filed Apr. 23, 2008 by Ethelfeld et al.
Final Office Action mailed Dec. 29, 2009 in U.S. Appl. No. 11/663,048, filed Nov. 15, 2007 by Thorkild et al.
Non-Final Office Action mailed Apr. 17, 2009 in U.S. Appl. No. 11/663,048, filed Nov. 15, 2007 by Thorkild et al.
Notice of Abandonment mailed Oct. 23, 2007 in U.S. Appl. No. 11/662,905, filed Sep. 22, 2005 by Ahm et al.
Non-Final Office Action mailed May 19, 2010 in U.S. Appl. No. 11/541,348, filed Sep. 29, 2006 by Preuthun et al.
Final Office Action mailed Jan. 8, 2010 in U.S. Appl. No. 11/541,348, filed Sep. 29, 2006 by Preuthun et al.
Non-Final Office Action mailed May 22, 2009 in U.S. Appl. No. 11/541,348, filed Sep. 29, 2006 by Preuthun et al.
Response and Amendment filed Jan. 29, 2009 in U.S. Appl. No. 11/541,348, filed Sep. 29, 2006 by Preuthun et al.
Final Office Action mailed Oct. 29, 2008 in U.S. Appl. No. 11/541,348, filed Sep. 29, 2006 by Preuthun et al.
Response and Amendment filed Jul. 16, 2008 in U.S. Appl. No. 11/541,348, filed Sep. 29, 2006 by Preuthun et al.
Non-Final Office Action mailed Apr. 18, 2008 in U.S. Appl. No. 11/541,348, filed Sep. 29, 2006 by Preuthun et al.
Final Office Action mailed May 5, 2010 in U.S. Appl. No. 11/540,842, filed Sep. 29, 2006 by Preuthun et al.
Non-Final Office Action mailed Sep. 28, 2009 in U.S. Appl. No. 11/540,842, filed Sep. 29, 2006 by Preuthun et al.
Response and Amendment filed Aug. 7, 2009 in U.S. Appl. No. 11/540,842, filed Sep. 29, 2006 by Preuthun et al.
Final Office Action mailed May 13, 2009 in U.S. Appl. No. 11/540,842, filed Sep. 29, 2006 by Preuthun et al.
Response and Amendment filed Mar. 11, 2009 in U.S. Appl. No. 11/540,842, filed Sep. 29, 2006 by Preuthun et al.
Non-Final Office Action mailed Dec. 12, 2008 in U.S. Appl. No. 11/540,842, filed Sep. 29, 2006 by Preuthun et al.
Response and Amendment filed Oct. 10, 2008 in U.S. Appl. No. 11/540,842, filed Sep. 29, 2006 by Preuthun et al.
Final Office Action mailed Jul. 11, 2008 in U.S. Appl. No. 11/540,842, filed Sep. 29, 2006 by Preuthun et al.
Response and Amendment filed May 20, 2008 in U.S. Appl. No. 11/540,842, filed Sep. 29, 2006 by Preuthun et al.
Non-Final Office Action mailed Feb. 25, 2008 in U.S. Appl. No. 11/540,842, filed Sep. 29, 2006 by Preuthun et al.
Final Office Action mailed Aug. 5, 2009 in U.S. Appl. No. 11/407,647, filed Apr. 20, 2006 by Hansen et al.
Non-Final Office Action mailed Feb. 6, 2009 in U.S. Appl. No. 11/407,647, filed Apr. 20, 2006 by Hansen et al.
Final Office Action mailed Sep. 29, 2008 in U.S. Appl. No. 11/407,647, filed Apr. 20, 2006 by Hansen et al.
Non-Final Office Action mailed Feb. 28, 2008 in U.S. Appl. No. 11/407,647, filed Apr. 20, 2006 by Hansen et al.
Notice of Abandonment mailed Oct. 12, 2010 in U.S. Appl. No. 11/266,904, filed Nov. 4, 2005 by Ethelfeld et al.
Second Advisory Action mailed Aug. 13, 2008 in U.S. Appl. No. 11/266,904, filed Nov. 4, 2005 by Ethelfeld et al.
First Advisory Action mailed Dec. 28, 2007 in U.S. Appl. No. 11/266,904, filed Nov. 4, 2005 by Ethelfeld et al.
Requirement for Restriction mailed May 22, 2006 in U.S. Appl. No. 11/266,904, filed Nov. 4, 2005 by Ethelfeld et al.
Notice of Allowance mailed Jul. 15, 2009 in U.S. Appl. No. 11/266,821, filed Nov. 4, 2005 by Ethelfeld et al.
Final Office Action mailed Oct. 16, 2009 in U.S. Appl. No. 11/250,233, filed Oct. 14, 2005 by Ethelfeld et al.
Non-Final Office Action mailed Mar. 12, 2009 in U.S. Appl. No. 11/250,233, filed Oct. 14, 2005 by Ethelfeld et al.
Notice of Abandonment mailed Aug. 31, 2010 in U.S. Appl. No. 10/566,795, filed Aug. 30, 2006 by Radmer et al.
Final Office Action mailed May 4, 2009 in U.S. Appl. No. 10/566,795, filed Aug. 30, 2006 by Radmer et al.
Non-Final Office Action mailed Oct. 17, 2008 in U.S. Appl. No. 10/566,795, filed Aug. 30, 2006 by Radmer et al.
US 6,197,009, 03/2001, Steg (withdrawn)

* cited by examiner

← 200

237  257

237

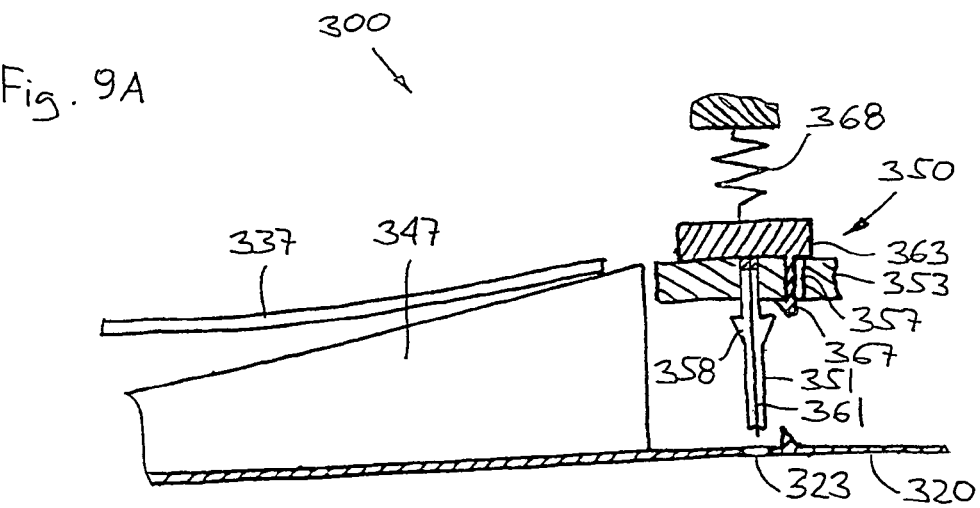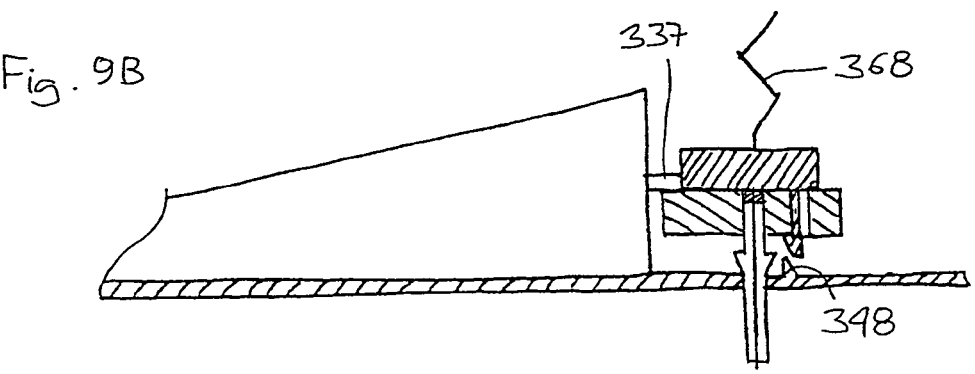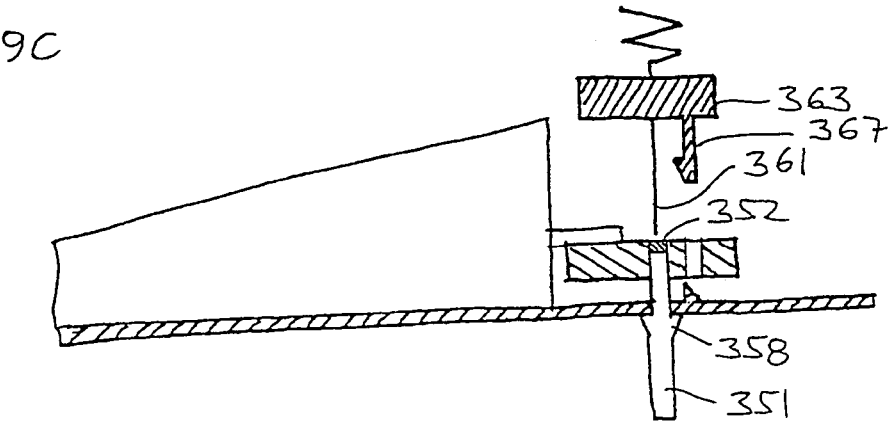

INTERNAL NEEDLE INSERTER

CROSS REFERENCE TO RELATED APPLICATIONS

This application is a continuation of international application no. PCT/DK2004/000333 filed May 10, 2004 and claims priority of Danish application no. PA 2003 00697 filed May 8, 2003 and U.S. provisional application No. 60/471,010 filed May 16, 2003, all of which are hereby incorporated by reference.

The present invention generally relates to the insertion of transcutaneous devices such as needles, needle-like members and cannulas. More specifically, the invention relates to insertion of a transcutaneous device at a selected site within the body of a subject for subcutaneous, intravenous, intramuscular or intradermal delivery of a drug to the subject, the transcutaneous device being carried by a device comprising a mounting surface adapted for application to the skin of the subject. Especially, the invention relates to insertion of an infusion needle or cannula for the infusion of a drug, to insertion of a needle-formed sensor, as well as to insertion of insertion needles for easy placement of a device such as a sensor through the skin of a subject.

BACKGROUND OF THE INVENTION

In the disclosure of the present invention reference is mostly made to the treatment of diabetes by injection or infusion of insulin, however, this is only an exemplary use of the present invention.

Portable drug delivery devices for delivering a drug to a patient are well known and generally comprise a reservoir adapted to contain a liquid drug and having an outlet in fluid communication with a hollow infusion needle, as well as expelling means for expelling a drug out of the reservoir and through the skin of the subject via the hollow needle. Such devices are often termed infusion pumps.

Basically, infusion pumps can be divided into two classes. The first class comprises durable infusion pumps which are relatively expensive pumps intended for 3-4 years use, for which reason the initial cost for such a pump often is a barrier to this type of therapy. Although more complex than traditional syringes and pens, the pump offer the advantages of continuous infusion of insulin, precision in dosing and optionally programmable delivery profiles and user actuated bolus infusions in connections with meals.

Addressing the above problem, several attempts have been made to provide a second class of drug infusion devices that are low in cost and convenient to use. Some of these devices are intended to be partially or entirely disposable and may provide many of the advantages associated with an infusion pump without the attendant cost and inconveniencies, e.g. the pump may be prefilled thus avoiding the need for filling or refilling a drug reservoir. Examples of this type of infusion devices are known from U.S. Pat. Nos. 4,340,048 and 4,552, 561 (based on osmotic pumps), U.S. Pat. No. 5,858,001 (based on a piston pump), U.S. Pat. No. 6,280,148 (based on a membrane pump), U.S. Pat. No. 5,957,895 (based on a flow restrictor pump (also know as a bleeding hole pump), U.S. Pat. No. 5,527,288 (based on a gas generating pump), or U.S. Pat. No. 5,814,020 (based on a swellable gel) which all in the last decades have been proposed for use in inexpensive, primarily disposable drug infusion devices, the cited documents being incorporated by reference.

The disposable pumps generally comprises a skin-contacting mounting surface adapted for application to the skin of a subject by adhesive means, and with the infusion needle arranged such that in a situation of use it projects from the mounting surface to thereby penetrate the skin of the subject, whereby the place where the needle penetrates the skin is covered while the appliance is in use.

The infusion needle may be arranged to permanently project from the mounting surface such that the needle is inserted simultaneously with the application of the infusion pump. Examples of this configuration can be found in U.S. Pat. Nos. 2,605,765, 4,340,048 and in EP 1 177 802. Although this configuration provides a simple and cost-effective solution, the actual user-performed piercing of the tissue with the needle is often problematic as people who are not experts in medicine are usually insufficiently practised to place such a needle correctly and they often suffer from a fear of the likely pain. Although not relating specifically to infusion pumps, U.S. Pat. No. 5,851,197 discloses an injector in which an infusion set comprising a skin-mountable surface with a protruding needle can be mounted, the injector upon actuation driving the entire infusion set into contact with a skin portion whereby the needle is inserted through the skin.

Addressing the above problem, infusion pump devices have been proposed in which the pump device is supplied to the user with the needle in a retracted state, i.e. with the distal pointed end of the needle "hidden" inside the pump device, this allowing the user to place the pump device on the skin without the possibility of observing the needle. When first the needle is hidden, at least some of the fear is overcome making the introduction of the needle in a second step less problematic. U.S. Pat. Nos. 5,858,001 and 5,814,020 disclose infusion devices of this type in which an infusion needle is arranged in an upper housing portion pivotably arranged relative to a base plate portion. In this way the user can introduce the needle by pressing the upper portion into engagement with the base plate portion.

To further reduce the fear and pain associated with the introduction of the needle, many recent pump devices have been provided with actuatable needle insertion means, which just has to be released by the user after which e.g. spring means quickly will advance the needle through the skin.

For example, U.S. Pat. No. 5,957,895 discloses a liquid drug delivery device comprising a bent injection needle which is adapted to project through a needle aperture in the bottom surface of the housing in a situation of use. A movable needle carrier is disposed in the housing for carrying the injection needle and for causing the injection end of the needle to project through the needle aperture upon movement of the needle carrier.

U.S. Pat. No. 5,931,814 discloses an infusion device having a housing with a drug reservoir, an infusion needle (or cannula) communicating with the reservoir, means for inserting the needle, and pump means for discharging the reservoir contents through the needle. The needle is fixed relative to the housing and projects beyond the lower skin-contacting surface of the housing to the depth required for injection. The needle is surrounded by a protective element which is moved by spring means from a first end position in which the protective device projects beyond the lower surface of the housing and beyond the needle to a second end position in which the protective device does not project beyond the underside of the casing. An advantage of this design is that the needle is arranged in a fixed position relative to the reservoir. WO 02/15965 discloses a similar infusion device in which a base plate member acts as a protecting element until an upper part of the device, to which the needle is fixed, is moved down into engagement with the base plate member.

In the devices disclosed in U.S. Pat. Nos. 5,957,895 and 5,931,814 the needle is automatically inserted by the release of pre-tensioned spring means arranged within the devices, whereas in the device known from WO 02/15965 the needle is inserted by the user actively moving the hidden needle. Although the automatic needle insertion means adds convenience for the user and may serve to overcome needle fear, such means also adds to the complexity and thus to the cost of the device, just as they may reduce the reliability.

Before turning to the disclosure of the present invention, a different type of device relying on the insertion of a needle or needle-like structure will be described.

Although drug infusion pumps, either disposable or durable, may provide convenience of use and improved treatment control, it has long been an object to provide a drug infusion system for the treatment of e.g. diabetes which would rely on closed loop control, i.e. being more or less fully automatic, such a system being based on the measurement of a value indicative of the condition treated, e.g. the blood glucose level in case of insulin treatment of diabetes.

A given monitor system for measuring the concentration of a given substance may be based on invasive or non-invasive measuring principles. An example of the latter would be a non-invasive glucose monitor arranged on the skin surface of a patient and using near-IR spectroscopy, however, the present invention is concerned with the introduction of a transcutaneous device such as a needle-formed sensor element.

The sensor may be placed subcutaneously being connected to external equipment by wiring or the substance (e.g. fluid) to be analysed may be transported to an external sensor element, both arrangements requiring the placement of a subcutaneous component (e.g. small catheter or tubing), the present invention addressing both arrangements. However, for simplicity the term "sensor" is used in the following for both types of elements introduced into the subject.

Turning to the sensor elements per se, relatively small and flexible electrochemical sensors have been developed for subcutaneous placement of sensor electrodes in direct contact with patient blood or other extra-cellular fluid (see for example U.S. Pat. No. 5,482,473), wherein such sensors can be used to obtain periodic or continuous readings over a period of time. Insertion devices for this type of sensors are described in, among others, U.S. Pat. Nos. 5,390,671, 5,391,950, 5,568,806 and 5,954,643 which hereby are incorporated by reference.

More specifically, U.S. Pat. No. 5,954,643 discloses an insertion set comprising a mounting base supporting a proximal end of a flexible thin film sensor, the sensor including a distal segment with sensor electrodes thereon which protrudes from the mounting base for transcutaneous placement, wherein the sensor distal segment is slidably carried by a slotted insertion needle fitted through the assembled base. Placement of the insertion set against the patient's skin causes the insertion needle to pierce the skin to carry the sensor electrodes to the desired subcutaneous site, after which the insertion needle can be slidably withdrawn from the insertion set. A similar arrangement is known from U.S. Pat. No. 5,568,806.

DISCLOSURE OF THE INVENTION

Having regard to the above-identified problems, it is an object of the present invention to provide a device comprising a transcutaneous device and insertion means (or driving means) therefore, which allows for easy and swift, automatic insertion of the transcutaneous device, yet is reliable in use. The device should be compact in size and be designed for cost effective manufacturing.

The present invention provides that the transcutaneous device insertion means can be activated by the user during actuation of the insertion means for the transcutaneous device. In this context the term "activation" of the insertion means relates to the energizing thereof, whereas the term "actuation" relates to the user-related input responsible for both energizing and release of the insertion means.

Correspondingly, a medical device is provided, comprising a housing having a mounting surface adapted for application to the skin of a subject, a transcutaneous device with a distal, pointed end portion adapted to penetrate the skin of the subject, wherein the transcutaneous device has a first position in which the distal end portion is retracted within the housing, and a second position in which the distal end portion projects relative to the mounting surface. The medical device further comprises actuatable driving means disposed within the housing and adapted to move the transcutaneous device from the first position to the second position when the driving means is actuated, wherein the driving means is actuatable from a first state through an intermediate state to a second state, whereby actuation of the driving means from the first to the intermediate state causes activation of the driving means, and actuation of the driving means from the intermediate to the second state causes release of the activated driving means thereby moving the transcutaneous device from the first position to the second position. As the device normally will be supplied to the user with the transcutaneous device in the first position, the first state may also be termed an initial state just as the second state may be termed an active state.

It should be emphasized that the activated state not necessarily is a stable state in which the spring means can be left, but a state which may require that an actuation input (e.g. a force applied by the user) is upheld, i.e. the spring means may resume an initial state if the actuation input is removed. Further, the actuation means may be partly energized in their initial state.

By this arrangement a medical device is provided which can be supplied to the user in a non-energized or only slightly energized state, the energizing taking place when the device is actuated by the user which means that energy will be stored only for a period from a few seconds to a few hours or days. For example, the device may be designed such that the drive means is fully depleted from energy when the transcutaneous device has been inserted (e.g. by locking the transcutaneous device in its second position), or it may be designed to exert a biasing force upon the transcutaneous device in its second position. In this way the drive means and the elements upon which a force is exerted by the drive means can be optimized for a very short "active" life, this in contrast to arrangements in which energy is stored corresponding to the entire shelf life of the device, e.g. one or more years. For example, much higher requirements would have to be fulfilled for a polymer spring adapted for storing energy during a period of several years, or by a polymer structure adapted for locking a metal spring during a corresponding period. Further, to prevent structures from locking (e.g. "growing together") during storage, it may be necessary to store additional energy to overcome a possible locking resistance, this adding to the aforementioned problems. Further again, by providing a device which can be shipped, stored and handled in a non-energized condition, the risk of accidental actuation will be reduced.

The transcutaneous device may be in the form of a pointed hollow infusion needle, a micro needle array, a pointed needle sensor, or a combination of a relatively flexible per se blunt cannula or sensor device with a pointed insertion needle may provide a pointed transcutaneous device, the insertion needle being retractable after insertion of the blunt portion of the transcutaneous device. The cannula is advantageously soft and flexible relative to the insertion needle which typically is a solid steel needle. In the disclosure of the present invention as well as in the description of the exemplary embodiments, reference will mostly be made to a transcutaneous device in the form of an infusion needle.

In exemplary embodiments the driving means comprises spring means adapted for releasably storing energy which can be activated respectively released when the driving means is actuated from the first state through the intermediate state to the second state by the user. The spring means may comprise any elastically compressible or deformable means, e.g. a metal or polymer member, an elastomeric foam or a gas. The driving means may be arranged to exert a force on at least a portion (e.g. in case the device comprises a retractable insertion needle) of the transcutaneous device in the second state thereby biasing it towards the second position. In exemplary embodiments the mounting surface comprises an aperture formed therein, the distal end portion of the transcutaneous device being moved through the aperture when the transcutaneous device is moved from the first to the second position.

The transcutaneous device may be provided as part of a unit (e.g. a needle unit) which is then engaged and moved by the driving means. Advantageously, the spring means comprises a drive portion adapted to engage an engagement portion of the transcutaneous device (i.e. the engagement portion may be part of the transcutaneous device or it may be associated therewith, e.g. by means of the aforementioned unit) when the spring means is released (e.g. the two portions actually coming into engagement with each other), wherein activation of the spring means causes an activation movement of the drive portion corresponding to the movement by which energy is releasably stored in the spring means, and a displacement movement, different from the activation movement, in which the drive portion and the engagement portion are moved relative to each other. In other words, when the user activates the spring means two actions take place: The spring is stressed and positioned relative to the portion of the needle unit which it is adapted to engage when released. The positioning may take place by moving the spring means, the needle unit or both. Advantageously the spring means will directly engage the needle or the structure carrying the needle, however, the needle unit may be provided with transfer or linkage means allowing the spring means to act indirectly on the needle, e.g. when it is desirable to transform a primary movement of the spring means such as from an upwards to a downwards movement.

The transcutaneous device may be introduced subcutaneously at any desired angel relative to the mounting surface (and thus the skin surface), e.g. in the second position the distal end portion may extend generally perpendicular to the mounting surface.

To provide a compact device, the drive portion corresponding to the first state may be arranged below and beside the engagement portion (with respect to the mounting surface), and such that the drive portion corresponding to the intermediate state is arranged in an upper position substantially above the engagement portion. By this arrangement release of the spring means causes downwards movement of the drive portion to engage the engagement portion whereby the needle is moved from the first position to the second position.

To allow the user to activate and release the drive means, the device advantageously comprises actuation means moveable from a first position through an intermediate position to a second position, whereby movement of the actuation means from the first to the intermediate position causes activation of the spring means, and movement from the intermediate to the second position causes release of the activated spring means thereby moving the needle from the first position to the second position. The actuation means may be in the form of user actuatable element which can be gripped or moved by the user relative to the housing (e.g. a button), or a (major) portion of the housing may be moveable relative to a base portion comprising the mounting surface. The movement preferably corresponds to a substantially non-composite movement (e.g. a unidirectional linear or rotational movement which may be with or without an intermediate lockable state). In an alternative arrangement actuation of the actuation means from the first through the intermediate to the second condition is accomplished by moving two actuation elements against each.

In an exemplary embodiment the spring means is coupled to the actuation means, whereby the displacement movement of the drive portion substantially corresponds to the movement of the actuation means from the first to the intermediate position.

Advantageously, the device comprises ramp (or lifting) means adapted to engage the spring means, such that movement of the actuation means from the first to the intermediate position causes the ramp means to move (lift) the drive portion to its upper position, and movement of the actuation means from the intermediate position to the second position causes the ramp means to disengage and thereby release the spring means. The spring means may comprise a spring member (e.g. a "physical" member such as a leaf spring or a "piano" string, this in contrast to a gas spring) having a proximal end mounted to the actuation means and a distal deflectable end portion comprising the drive portion, the distal end portion engaging the ramp means.

In an exemplary embodiment, the needle unit comprises a needle carrier carrying the needle, the needle carrier being coupled (e.g. pivotally) to the housing for controlled movement of the needle between the first and second positions.

In a further embodiment the first unit comprises a transcutaneous device comprising a transcutaneous member (e.g. a soft cannula or a sensor) in combination with a co-axially or co-linearly arranged pointed insertion needle, the insertion needle and the transcutaneous member being arranged to be simultaneously moved by the driving means from their respective first position to their respective second position when the driving means is actuated, wherein the insertion needle is arranged to be moveable away from the distal end of the transcutaneous member when the cannula and the insertion needle have been moved to their second position. Advantageously spring means is provided for automatically moving the insertion needle when the combined transcutaneous device has been advanced to the second position.

As indicated above, the present invention may be utilized in combination with a number of different types of devices.

For example, for a medical device as described above the needle may be in the form of a hollow infusion needle, the first unit further comprising a reservoir adapted to contain a liquid drug and comprising in a situation of use an outlet in fluid communication with the infusion needle, as well as expelling means for expelling a drug out of the reservoir and through the skin of the subject via the hollow needle. The reservoir and the expelling means may be of any suitable type, e.g. of any of the types described in the above-referred documents. The reservoir may be connected to the actuation means, and arranged such that movement of the actuation means between the first and the second position causes the reservoir to be arranged in fluid communication with the infusion needle. Advantageously, movement of the actuation means between the first and the second position causes actuation of the expelling means.

The needle may also be in the form of a needle sensor comprising sensor means capable of being influenced by a body substance and producing a signal corresponding thereto. The sensor means may be of any suitable type, e.g. of any of the types described in the above-referred documents.

In a further embodiment the first unit comprises an additional needle-formed member having a distal end, the needle-formed member having a first retracted position relative to the second unit, and a second position in which the distal end projects relative to the second unit, wherein the needle is in the form of a removable insertion needle arranged co-axially with and supporting the needle-formed member, the insertion needle and the needle-formed member being arranged to be simultaneously moved by the driving means from their respective first position to their respective second position when the driving means is actuated. Corresponding to the first and second specific aspects the insertion needle may be fixed or moveable relative to the mounting surface. The insertion needle may have any desirable configuration such as solid or grooved.

For any of the above-described embodiments, the mounting surface advantageously comprises adhesive means for adhering the first unit to the skin of the subject.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. Correspondingly, the term "subcutaneous infusion" is meant to encompass any method in which a needle device is inserted at a selected site within the body of a patient for subcutaneous, intravenous, intramuscular or intradermal delivery of a drug to a subject. Further, the term needle or needle device (when not otherwise specified) defines a piercing member (including an array of micro needles) adapted to be introduced into or through the skin of a subject.

BRIEF DESCRIPTION OF THE DRAWINGS

In the following the invention will be further described with references to the drawings, wherein FIGS. 9A-9C show in a schematic representation an embodiment of a cannula and insertion needle combination implemented in a device.

In the figures like structures are identified by like reference numerals.

DESCRIPTION OF EXEMPLARY EMBODIMENTS

When in the following terms as "upper" and "lower", "right" and "left", "horizontal" and "vertical" or similar relative expressions are used, these only refer to the appended figures and not to an actual situation of use.

FIGS. 1-3 show in schematic representations perspective views of different states of use of a medical device in accordance with the invention. Correspondingly, the configuration of the different structures as well as there relative dimensions are intended to serve illustrative purposes only.

Figure 1A:
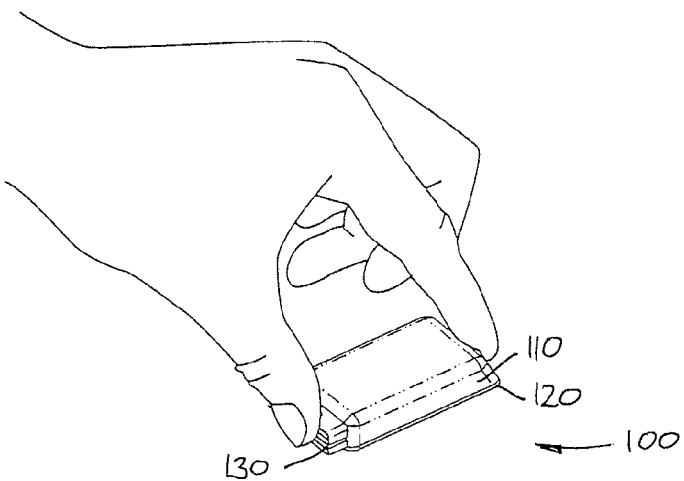
FIG. 1A shows in a perspective view a first embodiment of a medical device gripped by a user corresponding to a first state of use.
Figure 1B:
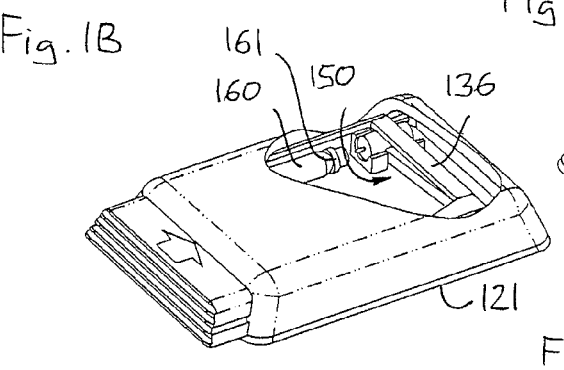
FIG. 1B shows the device of FIG. 1A with a portion of the housing cut off.
Figure 1D:
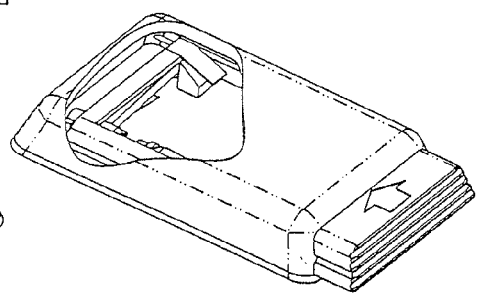
FIG. 1D shows the device of FIG. 1A seen from a different angle with a portion of the housing cut off.
Figure 1C:
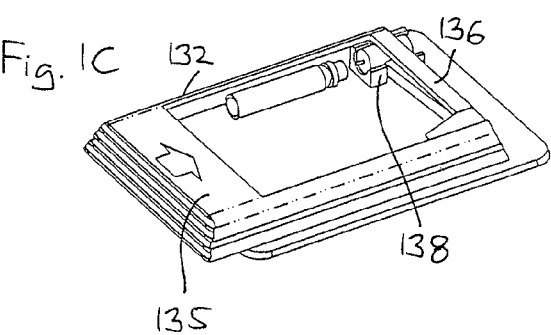
FIG. 1C shows the device of FIG. 1A with a portion of the housing removed.
Figure 1E:
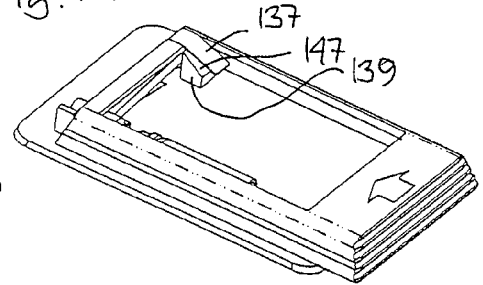
FIG. 1E shows the device of FIG. 1D with a portion of the housing removed.
Figure 2A:
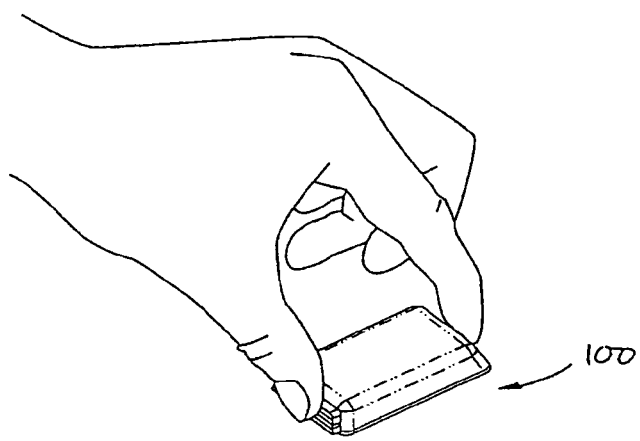
FIGS. 2A-2E shows an intermediate state of use corresponding to FIGS. 1A-1E.
Figure 2B:
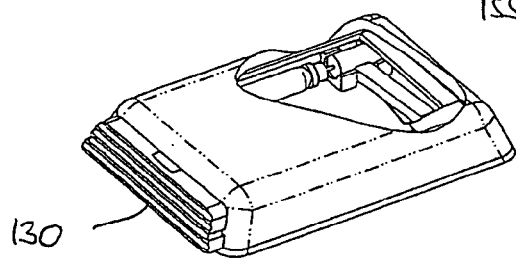
Figure 2D:
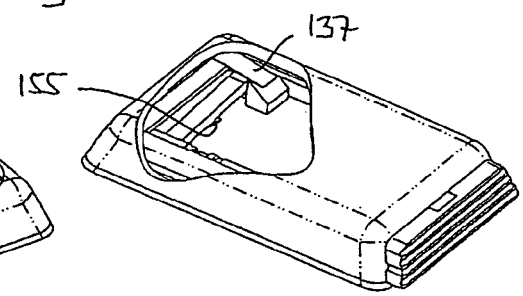
Figure 2C:
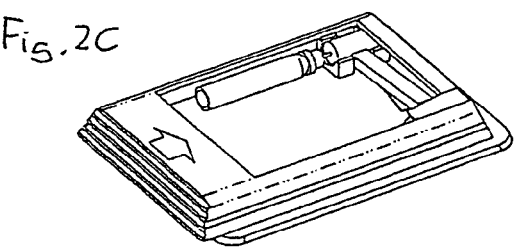
Figure 2E:
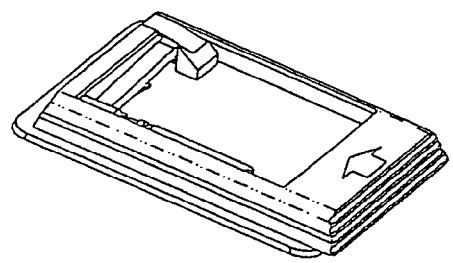
Figure 3A:
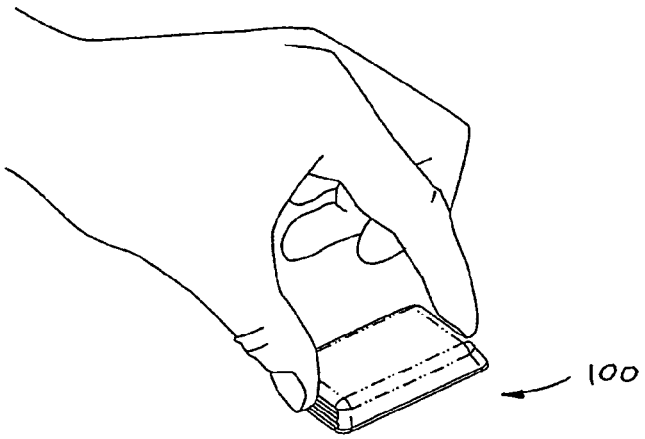
FIGS. 3A-3E shows a second state of use corresponding to FIGS. 1A-1E.
Figure 3B:
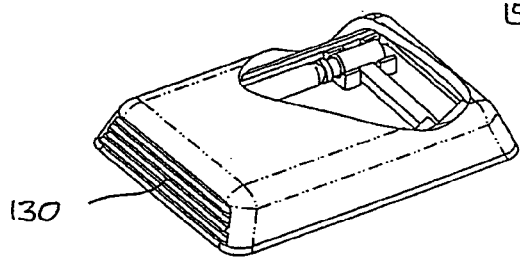
Figure 3D:
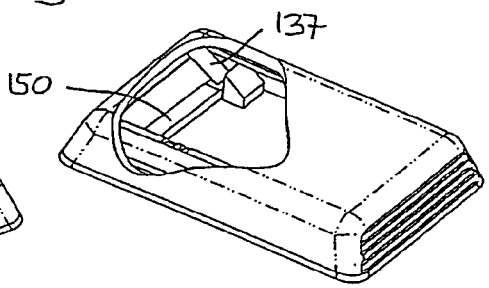
Figure 3C:
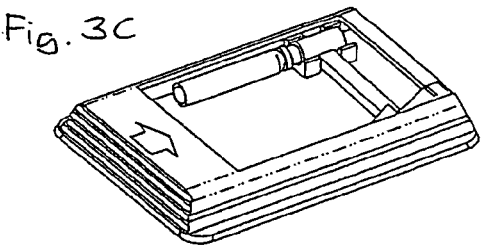
Figure 3E:
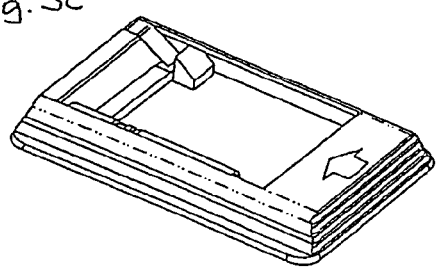
Figure 4A:
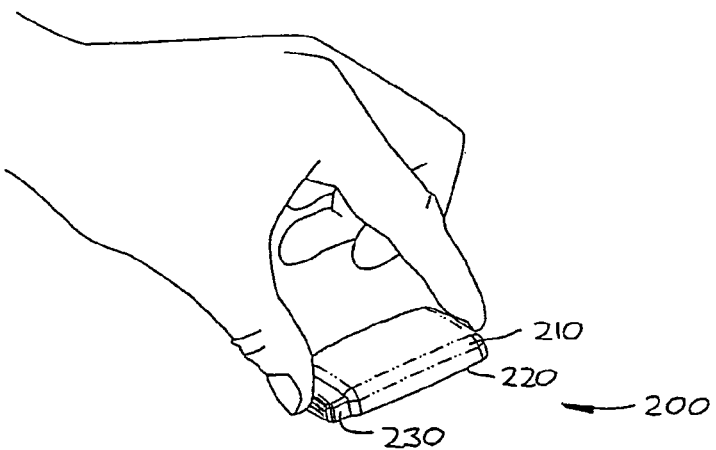
FIG. 4A shows in a perspective view a second embodiment of a medical device gripped by a user corresponding to a first state of use.
Figure 4B:
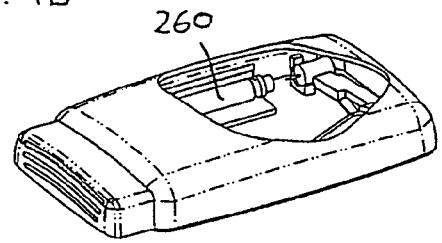
FIG. 4B shows the device of FIG. 4A with a portion of the housing cut off.
Figure 4D:
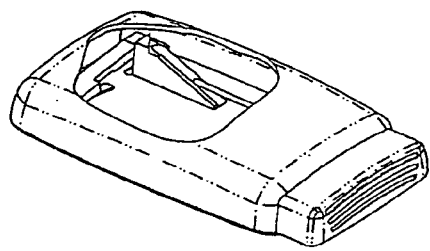
FIG. 4D shows the device of FIG. 4A seen from a different angle with a portion of the housing cut off.
Figure 4C:
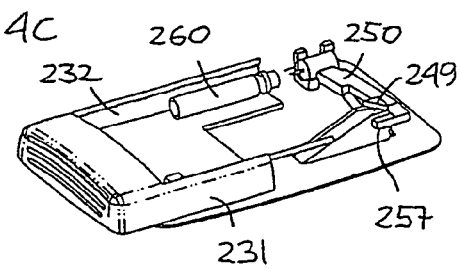
FIG. 4C shows the device of FIG. 4A with a portion of the housing removed.
Figure 4E:
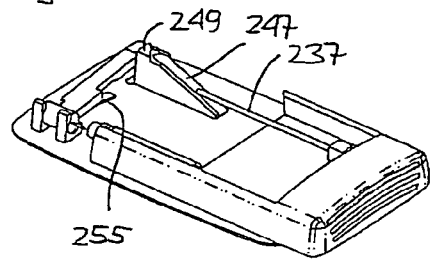
FIG. 4E shows the device of FIG. 4D with a portion of the housing removed.
Figure 5A:
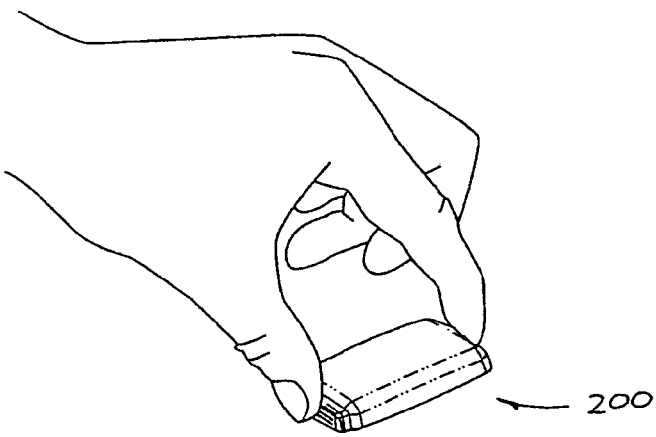
FIGS. 5A-5E shows an intermediate state of use corresponding to FIGS. 4A-4E.
Figure 5B:
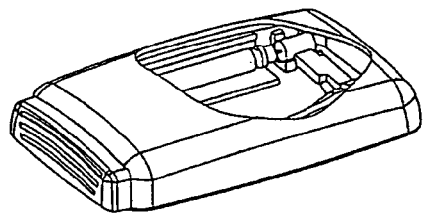
Figure 5D:
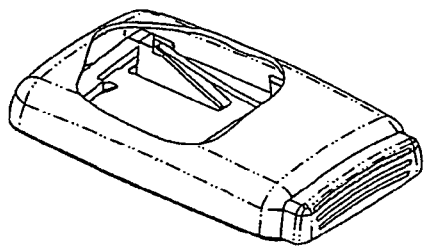
Figure 5C:
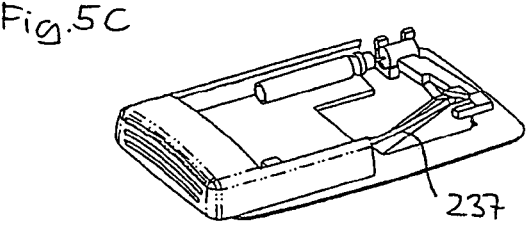
Figure 5E:
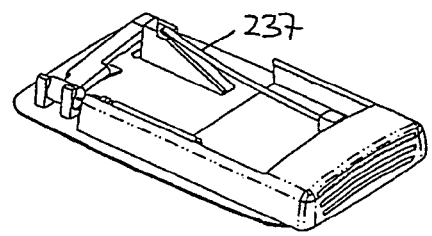
Figure 6A:
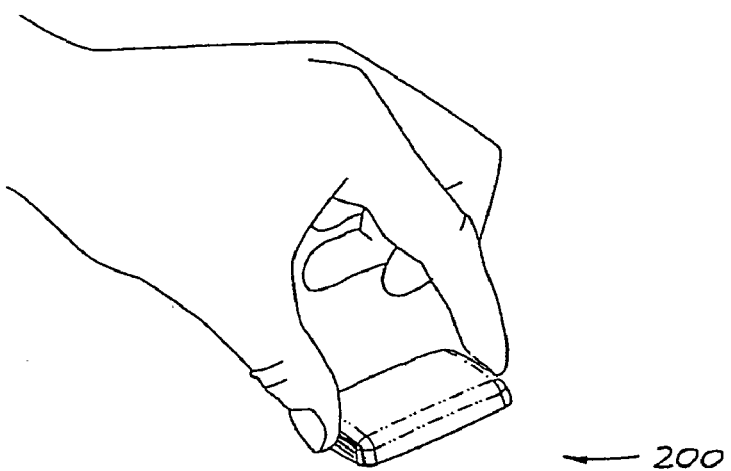
FIGS. 6A-6E shows a second state of use corresponding to FIGS. 4A-4E.
Figure 6B:
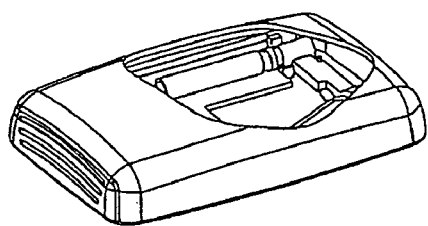
Figure 6D:
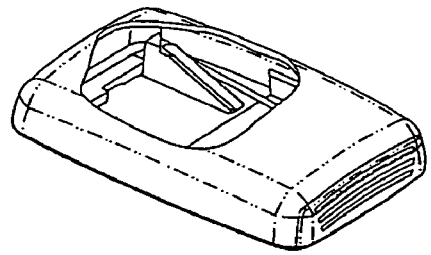
Figure 6C:
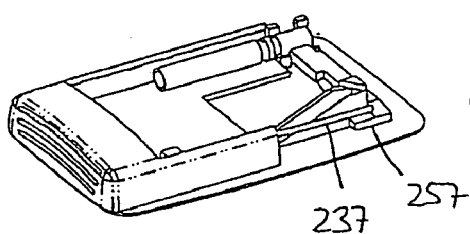
Figure 6E:
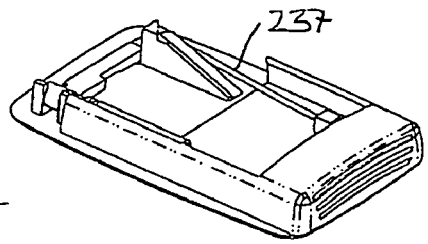

More specifically, FIG. 1A shows a first embodiment of a medical device 100 gripped by a user. The medical device comprises a housing with an upper housing portion 110 and a lower base plate portion 120, the housing providing a cavity in which an actuation member 130 is slidingly received through an opening, the actuation element being moveable corresponding to a longitudinal direction in respect of the device. The base plate portion comprises an adhesive mounting surface 121 adapted for application to the skin of a subject, the mounting surface being generally planar and defining a general plane. The actuation member comprises a ribbed area allowing for easy gripping by a user, e.g. using the first and second fingers as shown.

In the shown embodiment the actuation member is formed as a frame having opposed side portions 131, 132 adapted to be in sliding engagement with inner surface portions of the upper housing portions, the inner surface portions comprising longitudinally ridges received in corresponding grooves formed on the outer surfaces of the side portions. The two side portions are connected by a button portion 135 corresponding to an outer end and by a bridge portion 136 corresponding to an inner end thereof, the bridge portion comprising a spring means in the form of a leaf spring 137 having a free end portion with an inclined orientation relative to the base plate portion, the leaf spring serving as an insertion spring. The leaf spring may be attached to the bridge portion (e.g. when made from a metal alloy) or it may be formed integrally with the actuation member (e.g. manufactured from a polymer). The base plate portion comprises an upper surface on which a female hinge member 138 and a ramp member 139 are formed, preferably formed integrally with the base plate portion. The ramp member comprises an upper inclined ramp surface 147 adapted to engage a lower surface of the leaf spring 137 (serving as a drive portion adapted to engage a corresponding engagement portion on the transcutaneous device), the ramp surface terminating in an upper free edge 148. Although not literally a ramp, the term "ramp" also covers the embodiment in which a narrow upstanding wall terminates in a free edge over which the leaf spring slides.

The device further comprises a transcutaneous device in the form of an infusion needle forming part of a needle unit 150 connected to the base plate portion by a hinge allowing the needle unit to pivot corresponding to a pivoting axis defined by the hinge, the pivoting axis being arranged substantially in parallel with the mounting surface. The needle unit comprises a hollow infusion needle (see FIG. 7) having a distal pointed outlet portion 151 adapted to penetrate the skin of the subject, the outlet portion extending generally perpendicular to the mounting surface, and a pointed proximal inlet portion 152 arranged substantially corresponding to the pivoting axis. The distal end may be straight or curved, e.g. arcuate corresponding to the pivoting axis. The needle is carried by a needle carrier comprising an arm portion 153 and a cylindrical male hinge portion, the needle carrier being connected to the female hinge member thereby forming the hinge. The arm comprises a biasing member in the form of a leaf spring 155 projecting therefrom, the spring being in engagement with the upper surface of the base plate member thereby providing an upwardly directed biasing force forcing the needle into its initial position.

By this arrangement the needle unit can pivot between an initial position in which the inlet portion of the needle is retracted within the housing, and a second position in which the inlet portion projects relative to the mounting surface through an opening (not to be seen in the figs.) formed in the base plate portion. In the disclosed embodiments the hinge is provided by cooperating members of the needle carrier respectively the housing, however, a "naked" needle may be connected to the housing or the needle carrier and the housing may be formed integrally connected to each other by a film-hinge.

The device further comprises a reservoir 160 adapted to contain a liquid drug and comprising in a situation of use an outlet in fluid communication with the infusion needle, and expelling means (not shown for better illustrating the principles of the invention) for expelling a drug out of the reservoir and through the skin of the subject via the hollow needle. The reservoir and the expelling means are mounted on the actuation member and thus moveable relative to the housing. The reservoir comprises a needle-penetratable septum 161 adapted to cooperate with the inlet portion of the infusion needle, the septum being arranged substantially corresponding to the pivoting axis, thereby allowing the needle unit to pivot substantially without non-rotational displacement of the inlet portion of the infusion needle relative to the septum.

With reference to FIGS. 2 and 3 use and actuation of the device 100 will be described.

After having placed the medical device on a skin portion, the user presses the actuation member 130 into the housing whereby the needle is inserted and the delivery means started. During this action the actuation member is moved from a first (initial) position through an intermediate position to a second position. During movement of the actuation member from the first to the intermediate position the insertion spring 137 is moved relative to the ramp member, this causing an upwards activation movement of the drive portion whereby energy is releasably stored in the spring, and a displacement movement in which the drive portion is moved to a position above the engagement portion of the needle unit. At the same time the reservoir is moved into fluid communication with the infusion needle. After this, actuation of the actuation member from the intermediate to the second position causes release of the activated spring (when the distal free edge of the insertion spring slides over the upper free edge of the ramp, whereby the insertion spring in a snap-action engages the needle unit thereby biasing it downwardly to its second position against the force of the biasing spring 155. At the same time the actuation member is locked in place by the insertion spring being locked behind the ramp member.

The delivery means or sensor electronics will have to be actuated in combination with insertion of the needle, either in combination with the above-described actuation of the needle (e.g. by closing an electric contact or by providing a fluid communication) or by using additional actuation means which may be operated separately after the device has been mounted on the skin and the needle introduced.

In FIGS. 4-6 is shown a second embodiment of a medical device 200 similar to the first embodiment, the device comprising an upper housing portion 210 and a lower base plate portion 220, the housing providing a cavity in which an actuation member 230 is slidingly received through an opening, the actuation element being moveable corresponding to a longitudinal direction. The device further comprises a reservoir 260 and a transcutaneous device in the form of an infusion needle forming part of a needle unit 250. The device also comprises an inserter spring 237 and a ramp member 247, however, in contrast to the first embodiment the inserter spring is in the form of a thin rod (or string) just as the ramp member is arranged to deflect the inserter spring upwards as well as sidewards.

More specifically, the ramp surface is somewhat longer and has a concave cross-sectional configuration, this allowing the rod spring to slide thereon without accidental disengagement. The ramp terminates in an obliquely oriented deflection wall 249 which will force the spring rod outwards when forced thereagainst. The rod may be formed integrally with the actuation member or attached as a separate member, e.g. as a metal string. The needle unit is similar to the first embodiment apart from comprising a separately formed engagement portion 257 projecting from the distal end of the carrier arm and arranged on the side of the ramp member just below the deflection wall. Further, in contrast to the first embodiment, the actuation member does not comprise a bridge portion connecting the inner ends of the side portions.

In use, the second embodiment is actuated in the same way as the first embodiment, the primary difference being that the insertion spring is released from the upper ramp surface by a sidewards movement provided by the deflection wall.

In the above described embodiments, the actuation member has been moved linearly, however, other movements may be utilized in accordance with the invention. For example, a medical device may have a circular configuration in which actuation may be provided by the user rotating an upper portion of the housing. In such an arrangement the insertion spring may extend radially with a free peripheral end sliding on a curved ramp.

FIG. 7A shows a needle unit 150 adapted to be connected to a housing member by a hinge allowing the needle unit to pivot corresponding to a pivoting axis defined by the hinge. More specifically, the needle unit comprises a needle carrier having a cylindrical hinge portion 154 defining the pivoting axis, and an arm member 153 extending perpendicularly from the hinge portion in respect of the pivoting axis. On a lower surface of the arm member a biasing means is arranged in the form of a leaf spring member 155 adapted to engage a portion of the housing. The needle carrier carries a needle having a distal pointed portion 151 adapted to penetrate the skin of the subject, the distal portion extending generally perpendicular to the mounting surface, and a proximal portion (152) arranged substantially corresponding to the pivoting axis. In this way the needle unit can be arranged to pivot between a first position in which the distal portion of the needle is retracted within a housing, and a second position in which the inlet portion projects relative to a mounting surface. In case the distal portion is in the form of cannula, the arm member may be provided with a needle-penetratable septum 159 allowing an insertion needle to be inserted through the cannula as shown in FIG. 9A. In the shown embodiment the carrier may be injection moulded around a needle, however, the carrier may also be formed from sheet metal to which a needle is attached e.g. by adhesive or welding.

In the above described embodiments, the transcutaneous device has been in the form of a unitary needle device (e.g. an infusion needle as shown or a needle sensor (not shown)), however, the transcutaneous device may also be in the form of a combination of cannula or a sensor in combination with an insertion needle which is withdrawn after insertion thereof.

Figure 7:
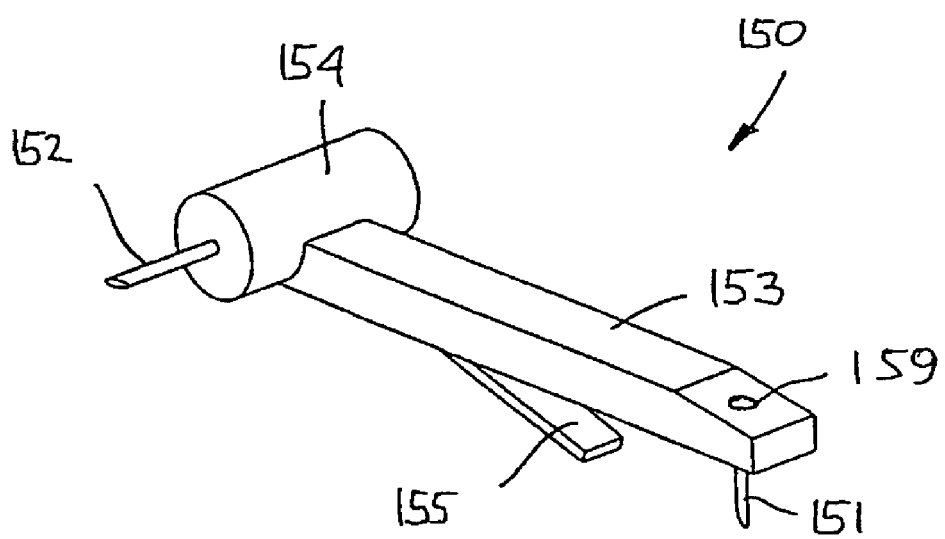
FIG. 7 shows a needle carrier.

Thus, FIGS. 9A-9C show in a schematic representation how a cannula and insertion needle combination can be implemented in a device 300 (partly shown) of the type described with reference to FIGS. 4-6. More specifically, a transcutaneous device unit 350 of the type shown in FIG. 7 is provided, however, in contrast to the needle unit 150 the transcutaneous device unit comprises a combination of a relatively soft cannula 351 (which e.g. may be of the soft "Teflon®" type) carried by a lower arm portion 353 and a pointed insertion needle 361 (e.g. made from medical grade stainless steel) slidably arranged within the cannula and carried by an upper arm portion 363, both arm portions being attached to a hinge portion (not shown). The lower arm further comprises a seal member 352 through which the insertion needle is arranged. The cannula and the insertion needle may be straight or curved, e.g. arcuate corresponding to the pivoting axis. The two arms comprise mating coupling means 367, 357 locking the arms together in an initial position with distal end of the insertion needle extending from the distal opening of the cannula as shown in FIG. 9A. The cannula is provided with locking means adapted to engage a base plate 320 of the device when the cannula has been moved to an extended position through an aperture 323 in the base plate. Between the housing of the device and the flexible arm a spring member 368 is arranged biasing the flexible arm upwards. Corresponding to the FIG. 4 embodiment, the device also comprises an inserter spring 337 and a ramp member 347, as well as an additional coupling release member 348.

In a situation of use the inserter spring is energized by being moved up the ramp by the user and then released to engage the lower arm to thereby pivot the transcutaneous device unit towards the extended position as shown in FIG. 9B. In its fully extended position the locking means of the cannula engages the housing of the device (here: an opening in the lower surface) and the coupling release member 348 engages the arm coupling means to thereby release the upper arm from the lower arm whereby the upper arm is moved towards its initial position by the spring member 368, thereby withdrawing the insertion needle from the cannula, see FIG. 9C. In the shown embodiment the cannula is irreversibly locked to the housing, however, advantageously releasable locking means is provided between the lower arm (or cannula) and the housing, this allowing the cannula to be withdrawn from its extended position before or after the used device is removed from the skin portion to which it has been attached, e.g. as illustrated in FIG. 10A.

Figure 10A:
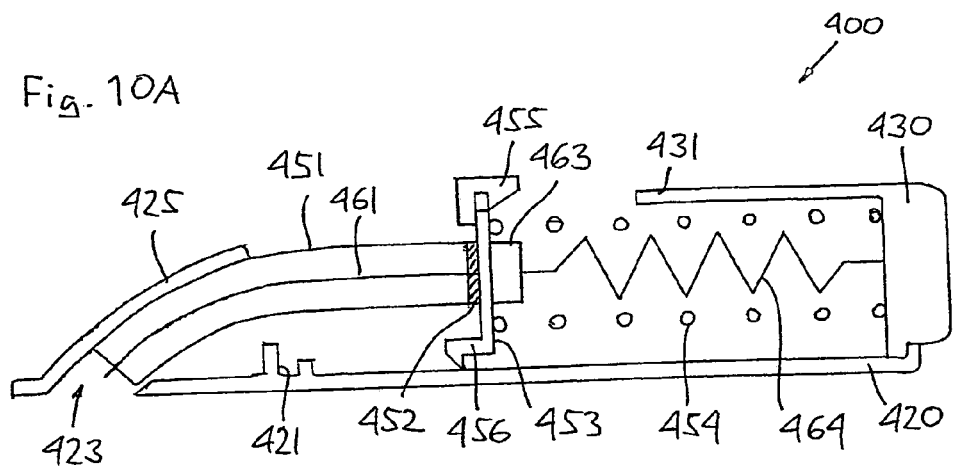
FIGS. 10A-10D show in a schematic representation a further embodiment a cannula and insertion needle combination implemented in a device.
Figure 10B:
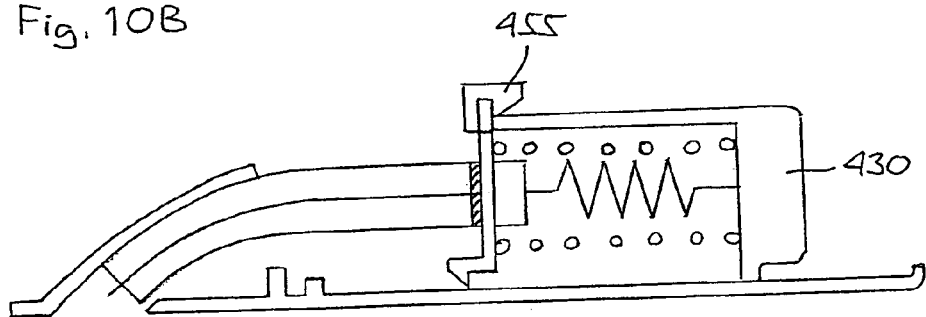

In FIGS. 10A-10D an alternative embodiment of a cannula and insertion needle arrangement is provided. More specifically, FIG. 10A shows in a schematic representation how a cannula and insertion needle combination can be implemented in a device having the same user functionality as the above-described devices but realized with different means. The device 400 (partly shown) comprises a housing in which a flexible, relatively soft cannula 451 (inlet not shown) (which e.g. may be of the soft "Teflon®" type) is mounted to a cannula carrier 453 with a locking catch 456, and a flexible pointed insertion needle 461 mounted to a needle carrier 463 and slidably arranged within the cannula through a sealing septum 452 is mounted. The device further comprises an actuation member 430 slidingly received in the housing of the device, the actuation element being moveable corresponding to a longitudinal direction in parallel with a lower base plate portion 420 comprising an opening 423 for the cannula, the actuation member comprising a release member 431. Between the actuation member and the cannula carrier a first spring 454 is arranged just as a second 464 spring is attached between the actuation member and the needle carrier. The housing is provided with a deflecting structure 425 for deflecting the cannula/insertion needle downwardly during insertion and for holding the cannula in that position, and a releasable catch member 455 holding the cannula carrier in its initial position against a slight biasing force of the first spring, the needle carrier being held in place against the cannula carrier by means of a slight biasing force of the second spring, the distal end of the insertion needle thereby extending from the distal opening of the cannula as shown in FIG. 10A.

Figure 10C:
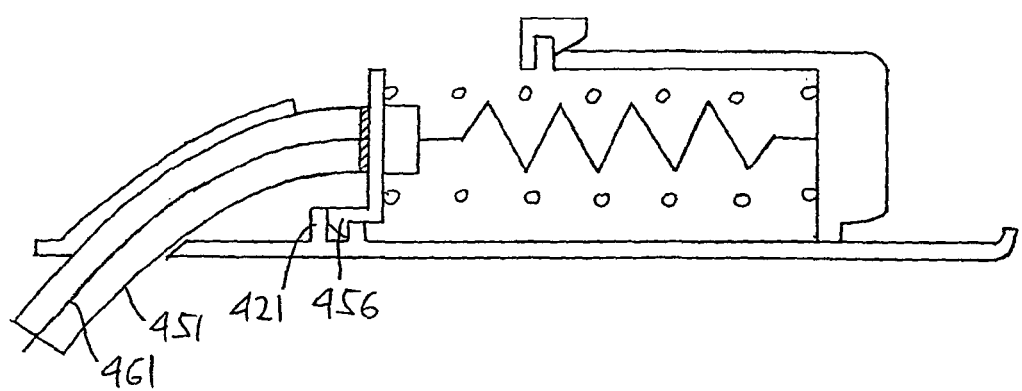
Figure 10D:
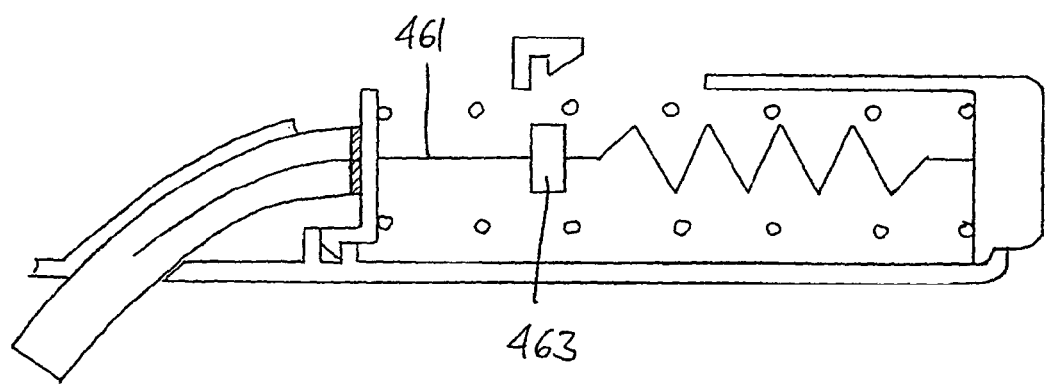

When a user actuates the actuation member the two springs are compressed corresponding to an intermediate state, however, as the actuation member reaches its fully actuated position the release member 431 releases the catch 455 (see FIG. 10B) which allows the two compressed springs to expand and thereby move the cannula and the insertion needle to their respective extended and downwardly deflected positions whereby the locking catch 456 engages a corresponding catch 421 in the housing as shown in FIG. 10C. When the user releases the actuation member the first spring expands to bias the actuation member towards its initial position, however, the second spring is shorter than the first spring such that it will withdraw the needle 461 from the cannula when the actuation member is released as shown in FIG. 10D.

For both of the above-described cannula embodiments, the relative dimensions of the different structures have been chosen for illustrative purposes only, especially, for a working embodiment the outer inner diameter of the cannula will correspond to the outer diameter of the insertion needle with only the minimum necessary clearance therebetween, this in order to provide a cannula with a small outer diameter.

In the above-described embodiments a medical device has been described comprising a reservoir, however, for better illustrating the principles of the present invention, the means for expelling a drug from the reservoir has been omitted in the figures. Such expelling means, which as the reservoir does not form part of the present invention in its basic form, may be of any type which would be suitable for arrangement within a skin-mountable drug delivery device. Further, as the needle of the present invention also may be in the form of a needle sensor, the interior of the medical device may comprise sensor means adapted to cooperate with the needle sensor.

Figure 8A:
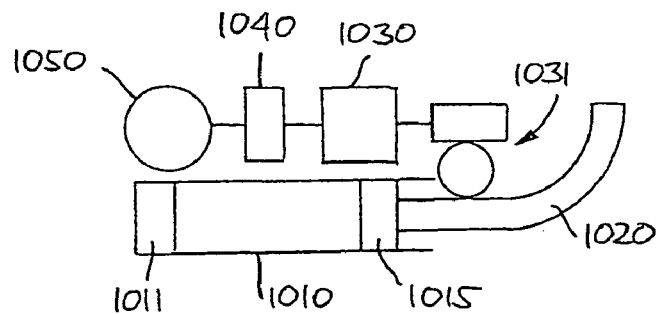
FIGS. 8A-8D shows different expelling means suitable for use with the invention.

In FIGS. 8A-8D examples of expelling means suitable for use with the present invention are shown schematically, however, these are merely examples. More specifically, FIG. 8A shows a pump arrangement comprising a drug-containing cartridge 1010 having a distal closure member 1011 allowing a needle to be connected, and a piston 1015 slidingly arranged there within, a flexible toothed piston rod 1020 (for example as disclosed in U.S. Pat. No. 6,302,869), an electric motor 1030 which via a worm-gear arrangement 1031 drives the piston rod to expel drug from the cartridge, the motor being controlled by control means 1040 and the energy for the control means and the motor being provided by a battery 1050. The pump may be activated when the needle is inserted (by means not shown) or by separate user-actuatable means (not shown) after the inserter has been detached form the delivery device.

Figure 8B:
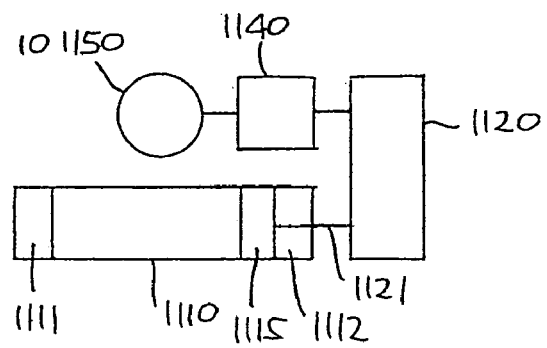

FIG. 8B shows a pump arrangement comprising a drug-containing cartridge 1110 having distal and proximal closure members 1111, 1112, and a piston 1115 slidingly arranged there within, gas generating means 1120 in fluid communication with the interior of the cartridge via conduit 1121 for driving the piston to expel drug from the cartridge, the gas generating means being controlled by control means 1140 and the energy for the control means and the gas generation being provided by a battery 1150. The pump may be activated as indicated above. A detailed disclosure of such gas generating means for a drug delivery device can be found in e.g. U.S. Pat. No. 5,858,001.

Figure 8C:
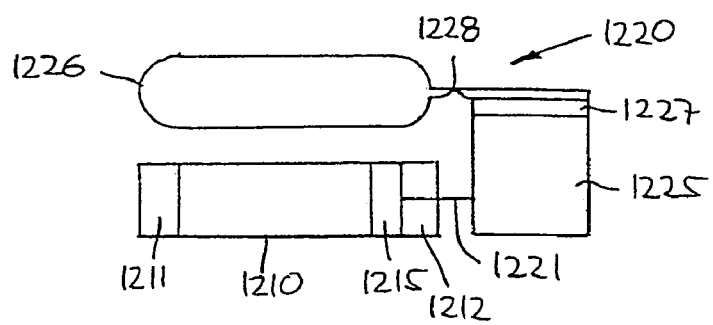

FIG. 8C shows a pump arrangement comprising a drug-containing cartridge 1210 having distal and proximal closure members 1211, 1212, and a piston slidingly 1215 arranged there within, an osmotic engine 1220 in fluid communication with the interior of the cartridge via conduit 1221 for driving the piston to expel drug from the cartridge. The osmotic engine comprises a first rigid reservoir 1225 containing a salt-solution and a second collapsible reservoir 1226 containing water, the two reservoirs being separated by a semi-permeable membrane 1227. When supplied to the user, the fluid connection 1228 between the second reservoir and the membrane is closed by a user-severable membrane (e.g. a weak weld) which, when severed, will allow the osmotic process to start as water is drawn from the second reservoir through the membrane and into the first reservoir. The pump may be activated as indicated above. A detailed disclosure of the osmotic drive principle can be found in e.g. U.S. Pat. No. 5,169,390.

Figure 8D:
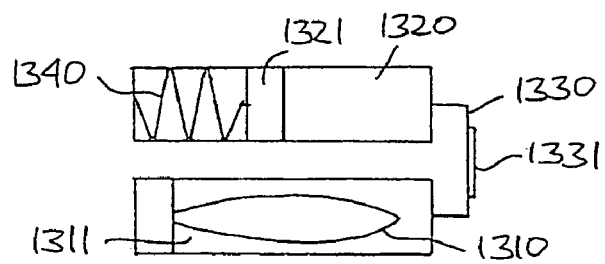

FIG. 8D shows a pump arrangement comprising a drug-containing flexible reservoir 1310 arranged within a rigid fluid-filled secondary reservoir 1311 in fluid communication with a primary reservoir 1320 through a conduit 1330 comprising a flow restrictor 1331. The primary reservoir is in the form of a cartridge with a moveable piston 1321 and contains a viscous drive fluid. A spring is arranged to act on the piston to drive fluid from the first to the second reservoir thereby expelling drug from the flexible reservoir when the latter is connected to an infusion needle (not shown). The flow rate will be determined by the pressure generated by the spring in the drive fluid, the viscosity of the drive fluid and the flow resistance in the flow restrictor (i.e. bleeding hole principle). The pump may be activated by straining the spring or by releasing a pre-stressed spring, either when the needle is inserted (by means not shown) or by separate user-actuatable means (not shown) after the inserter has been detached form the delivery device. An example of this principle used for drug infusion is known from DE 25 52 446. In an alternative configuration, the drug reservoir may be pressurized directly to expel the drug via a flow restrictor, e.g. as disclosed in U.S. Pat. No. 6,074,369.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

\* \* \* \* \*

CITED DOCUMENTS THAT ARE HEREBY INCORPORATED BY REFERENCE

U.S. Pat. No. 4,340,048
U.S. Pat. No. 4,552,561
U.S. Pat. No. 5,858,001
U.S. Pat. No. 6,280,148
U.S. Pat. No. 5,957,895
U.S. Pat. No. 5,527,288
U.S. Pat. No. 2,605,765
U.S. Pat. No. 4,340,048
EP 1 177 802
U.S. Pat. No. 5,814,020
U.S. Pat. No. 5,931,814
WO 02/15965
U.S. Pat. No. 5,482,473
U.S. Pat. No. 5,390,671
U.S. Pat. No. 5,391,950
U.S. Pat. No. 5,568,806
U.S. Pat. No. 5,954,643

The invention claimed is:

1. A medical device comprising:
   a housing having a mounting surface adapted for application to the skin of a subject,
   a transcutaneous device with a distal pointed end portion adapted to penetrate the skin of the subject,
   the transcutaneous device having a first position in which the distal end portion is retracted within the housing, and a second position in which the distal end portion projects relative to the mounting surface,
   a user actuatable driver disposed within the housing and the driver adapted to move the transcutaneous device from the first position to the second position when the driver is actuated,
   wherein the driver, with the transcutaneous device arranged in the first position, is actuatable from a first state through an intermediate state to a second state,
   whereby actuation of the driver from the first state to the intermediate state causes activation of the driver, and actuation of the driver from the intermediate state to the second state causes release of the activated driver thereby moving the transcutaneous device from the first position to the second position.

2. A medical device according to claim 1, wherein the driver comprises a spring means.

3. A method of operating a medical device, the method comprising:
   providing a housing having a mounting surface adapted for application to the skin of a subject,
   providing a transcutaneous device with a distal pointed end portion adapted to penetrate the skin of the subject, the transcutaneous device having a first position in which the distal end portion is retracted within the housing, and a second position in which the distal end portion projects relative to the mounting surface, providing a user actuatable driver disposed within the housing and adapted to move the transcutaneous device from the first position to the second position when the driver is actuated, actuating the driver when the transcutaneous device is arranged in the first position, by moving the driver from a first state through an intermediate state to a second state, whereby actuation of the driver from the first state to the intermediate state causes activation of the driver, and actuation of the driver from the intermediate state to the second state causes release of the activated driver thereby moving the transcutaneous device from the first position to the second position.

4. The method according to claim 3, wherein the method further comprises the medical device driver having a spring means.

* * * * *